(12) United States Patent
Fujii et al.

(10) Patent No.: US 8,093,434 B2
(45) Date of Patent: Jan. 10, 2012

(54) CRYSTAL POLYMORPH OF FLUORENE DERIVATIVE AND PRODUCTION METHOD THEREOF

(75) Inventors: Katsuhiro Fujii, Osaka (JP); Kota Fukui, Osaka (JP)

(73) Assignee: Taoka Chemical Company, Limited, Osaka (JP)

( * ) Notice: Subject to any disclaimer, the term of this patent is extended or adjusted under 35 U.S.C. 154(b) by 236 days.

(21) Appl. No.: 12/527,273

(22) PCT Filed: Feb. 1, 2008

(86) PCT No.: PCT/JP2008/052082
§ 371 (c)(1),
(2), (4) Date: Nov. 13, 2009

(87) PCT Pub. No.: WO2008/099765
PCT Pub. Date: Aug. 21, 2008

(65) Prior Publication Data
US 2010/0105961 A1    Apr. 29, 2010

(30) Foreign Application Priority Data
Feb. 15, 2007 (JP) ................................ 2007-034370

(51) Int. Cl.
*C07C 43/21* (2006.01)
(52) U.S. Cl. ........................................................ 568/633
(58) Field of Classification Search .................. 568/632, 568/633
See application file for complete search history.

(56) References Cited

U.S. PATENT DOCUMENTS
5,629,456 A * 5/1997 Yamada et al. ................ 568/633
2007/0100170 A1 * 5/2007 Murase et al. ................ 568/633

FOREIGN PATENT DOCUMENTS
| JP | 10-45656 A | | 2/1998 |
| JP | 10045655 | * | 2/1998 |
| JP | 2005-104898 A | | 4/2005 |
| JP | 2007-23016 A | | 2/2007 |

OTHER PUBLICATIONS
Journal of Applied Polymer Science (1995), 58, p. 1189-1197.*
Database CAPLUS on STN, Acc. No. 1998:59325, Yamada et al., JP 10017517 A (Jan. 20, 1998) (abstract).*

* cited by examiner

*Primary Examiner* — Brian J Davis
(74) *Attorney, Agent, or Firm* — Birch, Stewart, Kolasch & Birch, LLP

(57) ABSTRACT

A method of producing a crystal polymorph of 9,9-bis(4-(2-hydroxyethoxy)phenyl)fluorene, comprising the steps of
  reacting fluorenone and 2-phenoxyethanol in the presence of a heteropolyacid,
  initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene,
  dissolving the crude product in at least one solvent selected from the group consisting of aromatic hydrocarbon solvents, ketone solvents and ester solvents, and
  initiating deposition of 9,9-bis(4-(2-hydroxyethoxy)phenyl)fluorene at 50° C. or higher.

11 Claims, 2 Drawing Sheets

CRYSTAL POLYMORPH OF FLUORENE DERIVATIVE AND PRODUCTION METHOD THEREOF

TECHNICAL FIELD

The present invention relates to a novel crystal polymorph of 9,9-bis(4-(2-hydroxyethoxy)phenyl)fluorene, and a method of producing the same.

BACKGROUND ART

Recently, fluorene derivatives such as 9,9-bis(4-(2-hydroxyethoxy)phenyl)fluorene and the like are promising as raw materials for producing polymers (for example, epoxy resins, polyesters, polyethers, polycarbonates and the like) excellent in heat resistance and transparency and having high refractive index, and expected as materials and raw materials of optical lenses, films, plastic optical fibers, optical disk platforms, heat resistant resins, engineering plastics and the like.

For producing thermally and optically excellent polymers in these applications, it is important that the molecular weight is high, the molecular weight distribution is narrow and the content of un-reacted monomers and oligomers is low, and it is desired that a raw material monomer 9,9-bis(4-(2-hydroxyethoxy)phenyl)fluorene is highly pure and excellent in reactivity. Thus, control of the purity of a raw material monomer, control of crystal form significantly influencing the reactivity and control of the melting point are important factors for obtaining a more excellent polymer. Further, for maintaining excellent performances in polymer production and carrying out more stable production, it is necessary to separately produce specific crystal forms capable of maintaining a constant quality.

As the method of producing 9,9-bis(4-(2-hydroxyethoxy)phenyl)fluorene, disclosed are a method of dehydration-condensing fluorenone and phenoxyethanol using sulfuric acid and thiols as catalysts (patent document 1) and a method of reacting 9,9-bis(4-hydroxyphenyl)fluorene and ethylene carbonate (non-patent document 1). We made an application of a novel production method (patent document 2) different from the above-described production method. Patent document 1 describes a method of purifying the compound according to the present invention and non-patent document 1 describes that the melting point of the compound according to the present invention is 126 to 128° C., however, there are until now known no information at all regarding maintenance of constant qualities, such as the presence of different crystal polymorphs of the compound, relation between different crystal polymorphs, methods of producing respective crystal polymorphs necessary for industrial operations, and the like.
(patent document 1) JP-A No. 7-165657
(patent document 2) JP-A No. 2007-23016
(non-patent document 1) Journal of Applied Polymer Science, 1995, Vol. 58, 1189-1197

DISCLOSURE OF THE INVENTION

The present invention has an object of providing a novel crystal polymorph of 9,9-bis(4-(2-hydroxyethoxy)phenyl)fluorene maintaining a constant quality and excellent as a polymer raw material, and providing a method of producing this crystal polymorph.

The present inventors have intensively investigated to solve the above-described problem, and resultantly found that 9,9-bis(4-(2-hydroxyethoxy)phenyl)fluorene includes a novel crystal polymorph showing a melt endotherm maximum by differential scanning calorimetry of 150° C. to 180° C. (hereinafter, referred to as polymorph B) in addition to a conventionally known crystal polymorph showing a melt endotherm maximum by differential scanning calorimetry of 100° C. to 130° C. (hereinafter, referred to as polymorph A), and further, the present inventors have found a production method for obtaining such polymorph B preferentially, leading to completion of the present invention.

That is, the present invention provides the following (1) to (11).

(1) A method of producing a crystal polymorph of 9,9-bis(4-(2-hydroxyethoxy)phenyl)fluorene, comprising the steps of reacting fluorenone and 2-phenoxyethanol in the presence of a heteropolyacid, initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene, dissolving the crude product in at least one solvent selected from the group consisting of aromatic hydrocarbon solvents, ketone solvents and ester solvents, and initiating deposition of 9,9-bis(4-(2-hydroxyethoxy)phenyl)fluorene at 50° C. or higher.

(2) The production method according to the article (1), wherein the reaction of fluorenone and 2-phenoxyethanol in the presence of a heteropolyacid is carried out under dehydration condition.

(3) The production method according to the article (1) or (2), wherein the heteropolyacid is a heteropolyacid containing, as constituent elements, phosphoric acid or silic acid, and at least one element selected from vanadium, molybdenum and tungsten.

(4) The production method according to any one of the articles (1) to (3), wherein the heteropolyacid is a heteropolyacid anhydride or previously dehydration-treated heteropolyacid.

(5) The production method according to any one of the articles (1) to (4), wherein the solvent is an aromatic hydrocarbon solvent.

(6) The production method according to any one of the articles (1) to (4), wherein the solvent is toluene or xylene.

(7) A crystal polymorph of 9,9-bis(4-(2-hydroxyethoxy)phenyl)fluorene, wherein the melt endotherm maximum by differential scanning calorimetry is 150 to 180° C.

(8) A crystal polymorph of 9,9-bis(4-(2-hydroxyethoxy)phenyl)fluorene, wherein the melt endotherm maximum by differential scanning calorimetry is 160 to 166° C.

(9) A crystal polymorph of 9,9-bis(4-(2-hydroxyethoxy)phenyl)fluorene, wherein the diffraction angle 2θ in a powder X-ray diffraction pattern by Cu—Kα line shows peaks at 12.3°, 13.5°, 16.1°, 17.9°, 18.4°, 20.4°, 21.0°, 23.4° and 24.1°.

(10) The crystal polymorph according to the article (9), wherein the maximum peak of the diffraction angle 2θ is 18.4°.

(11) A crystal polymorph of 9,9-bis(4-(2-hydroxyethoxy)phenyl)fluorene, obtained by reacting fluorenone and 2-phenoxyethanol in the presence of a heteropolyacid, initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene, dissolving the crude product in at least one solvent selected from the group consisting of aromatic hydrocarbon solvents, ketone solvents and ester solvents, and initiating deposition of 9,9-bis(4-(2-hydroxyethoxy)phenyl)fluorene at 50° C. or higher.

MODES FOR CARRYING OUT THE INVENTION

Figure 1:
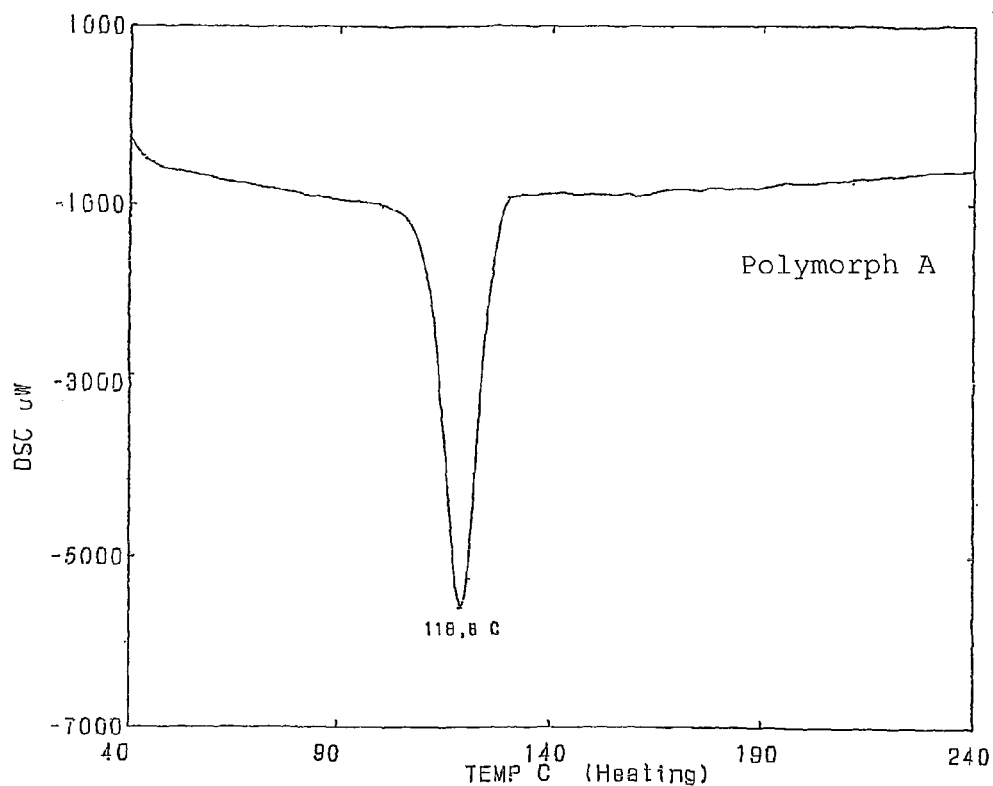
FIG. 1 is a view showing a differential scanning calorimetry (DSC) curve of a crystal (polymorph A) obtained in Comparative Example 1.

First, the method of reacting fluorenone and 2-phenoxyethanol in the presence of a heteropolyacid, then, initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene will be described.

The heteropolyacid used in the present invention is, in general, a collective designation for compounds produced by condensation of two or more different inorganic oxyacids, and various heteropolyacids can be produced by a combination of a center oxy acid and other oxy acids to be condensed around this. A minor number of elements forming the center oxy acid are called a hetero element, and elements forming oxy acids to be condensed around this are called a poly element. The poly element may be composed of a single kind of element or of several kinds of elements.

The hetero elements of oxyacids constituting the heteropolyacid are not particularly restricted, and examples thereof include copper, beryllium, boron, aluminum, carbon, silicon, germanium, tin, titanium, zirconium, cerium, thorium, nitrogen, phosphorus, arsenic, antimony, vanadium, niobium, tantalum, chrome, molybdenum, tungsten, uranium, selenium, tellurium, manganese, iodine, iron, cobalt, nickel, rhodium, osmium, iridium and platinum. Preferable is phosphorus or silicon. The poly elements of oxyacids constituting the heteropolyacid are not particularly restricted, and examples thereof include vanadium, molybdenum, tungsten, niobium and tantalum. Preferable are vanadium, molybdenum and tungsten.

As the heteropolyacid anion constituting the heteropolyacid skeleton, those of various compositions can be used. For example, $XM_{12}O_{40}$, $XM_{12}O_{42}$, $XM_{18}O_{62}$, $XM_6O_{24}$ and the like are mentioned. The preferable heteropolyacid anion composition is $XM_{12}O_{40}$. In the formulae, X represents a hetero element and M represents a poly element. Specifically exemplified as the heteropolyacids having these compositions are phosphomolybdic acid, phosphotungstic acid, silicomolybdic acid, silicotungstic acid, phosphovanadomolybdic acid and the like.

The heteropolyacid may be a free heteropolyacid, or part or all of protons may be substituted by other cations to give heteropolyacid salts to be used. Therefore, the heteropolyacid referred to in the present invention includes also these heteropolyacid salts. As the cations which can be substituted for protons, for example, ammonium, alkali metals, alkaline earth metals and the like are mentioned.

The heteropolyacid may be an anhydride or a crystal water-containing substance, however, the anhydride shows a quicker reaction and generation of by-products thereof is suppressed, thus, the anhydride is preferable. In the case of the crystal water-containing substance, the same effect as that of the anhydride can be obtained by previously performing dehydration treatments such as drying under reduced pressure, azeotropic dehydration with a solvent, and the like. The heteropolyacid may also be used in the form of being supported on a carrier such as activated carbon, alumina, silica-alumina, diatomaceous earth and the like. These heteropolyacid may be used singly, or two or more of them can be used in combination. If necessary, other catalysts than the heteropolyacid may also be used together in a range not deteriorating the object of the present invention.

Though the use amount of the heteropolyacid is not particularly restricted, it is 0.0001-fold by weight or more, preferably 0.001 to 30-fold by weight, further preferably 0.01 to 5-fold by weight with respect to fluorenone, for obtaining a sufficient reaction speed.

Though the use amount of 2-phenoxyethanol is not particularly restricted, it is usually 2 to 50 mol, preferably 2.5 to 20 mol, further preferably 3 to 10 mol with respect to 1 mol of fluorenone, from the standpoint of suppression of side reactions and of economy. Further, 2-phenoxyethanol can be used also as a reaction solvent.

Though the method of carrying out the reaction of fluorenone and 2-phenoxyethanol is not particularly restricted, it can be usually performed by charging fluorenone, 2-phenoxyethanol and heteropolyacid in a reaction apparatus, and heating them with stirring in air or under an atmosphere of an inert gas such as nitrogen, helium and the like, in the presence or absence of an inert solvent such as toluene, xylene and the like. In this operation, by carrying out the reaction under dehydration condition for removal of water in the reaction system such as catalyst-containing water, reaction-generated water and the like, the reaction progresses more quickly, production of by-products is suppressed and the targeted substance can be obtained with higher yield, than in the case of no dehydration. Thought the dehydration method is not particularly restricted, there are mentioned, for example, dehydration by addition of a dehydrating agent, dehydration by pressure reduction, dehydration by azeotrope with a solvent under normal pressure or reduced pressure, and the like.

Thought the dehydrating agent to be used in the reaction is not particularly restricted, mentioned are molecular sieve, sodium sulfate, magnesium sulfate and the like. Though the use amount of the dehydrating agent is not particularly restricted, it is usually 0.0001-fold by weight or more, preferably 0.001 to 100-fold by weight, further preferably 0.01 to 50-fold by weight with respect to fluorenone, from the standpoint of dehydration effect and economy.

Thought the azeotropic dehydration solvent to be used in the reaction is not particularly restricted, and there are mentioned aromatic hydrocarbon solvents such as toluene, xylene and the like, halogenated aromatic hydrocarbon solvents such as chlorobenzene, dichlorobenzene and the like, aliphatic hydrocarbon solvents such as pentane, hexane, heptanes and the like, halogenated aliphatic hydrocarbon solvents such as dichloromethane, 1,2-dichloroethane and the like, aliphatic and cyclic ether solvents such as diethyl ether, di-iso-propyl ether, methyl t-butyl ether, diphenyl ether, tetrahydrofuran, dioxane and the like, ester solvents such as ethyl acetate, butyl acetate and the like, nitrile solvents such as acetonitrile, propionitrile, butyronitrile, benzonitrile and the like, amide solvents such as N,N-dimethylformamide, N,N-dimethylacetamide, 1-methyl-2-pyrrolidone and the like. Preferable are aromatic hydrocarbon solvents and halogenated aromatic hydrocarbon solvents, and further preferable are toluene, xylene, chlorobenzene and dichlorobenzene. Though the use amount thereof is not particularly restricted, it is usually 0.1-fold by weight or more, preferably 0.5 to 100-fold by weight, further preferably 1 to 20-fold by weight with respect to fluorenone, from the economical standpoint.

Thought the reaction temperature varies depending on the kinds of raw materials and solvent to be used, it is usually 50 to 300° C., preferably 80 to 250° C., further preferably 120 to 180° C. The reaction can be traced by an analysis means such as liquid chromatography and the like.

After the reaction, the resultant reaction mixture may be left as it is at lower than 50° C. to deposit 9,9-bis(4-(2-hydroxyethoxy)phenyl)fluorene, however, usually, post treatments such as washing, concentration, dilution, treatment with activated carbon, and the like are performed before depositing 9,9-bis(4-(2-hydroxyethoxy)phenyl)fluorene at lower than 50° C. The operation of depositing 9,9-bis(4-(2-hydroxyethoxy)phenyl)fluorene from the reaction mixture subjected if necessary to the above-described post treatments is carried out by adjusting the reaction mixture mixed if necessary with a solvent to a temperature of 50° C. or higher and not higher than the boiling point of the solvent (preferably, 70 to 110° C.) and then cooling this to lower than 50° C. In the case of deposition of a crystal of 9,9-bis(4-(2-hydroxyethoxy)phenyl)fluorene from the reaction mixture at 50° C. or higher, the operation may advantageously be performed by mixing the reaction mixture with a dilution solvent in an amount preventing deposition of the crystal at 50° C. or higher, then, adjusting the resultant reaction mixture to a temperature of 50° C. or higher and not higher than the boiling point of the solvent (preferably, 70 to 110° C.) and then cooling this to lower than 50° C. Mentioned as the dilution solvent are those exemplified as the solvent to be used in the above-described reaction, and alcohol solvents such as methanol, ethanol, propanol, isopropanol, butanol, t-butanol, isobutanol, pentanol and the like; etc.

The temperature at the end of the cooling is not particularly restricted providing it is lower than 50° C., and it is usually −20 to 49° C., preferably 0 to 40° C., more preferably 10 to 30° C. Also the cooling speed is not particularly restricted, and it is usually 0.01 to 2° C., preferably 0.1 to 0.5° C., per minute. During the cooling, a crystal of 9,9-bis(4-(2-hydroxyethoxy)phenyl)fluorene may be added as a seed crystal into the reaction mixture. Such a crystal is usually a polymorph A.

The deposited crystal is recovered by filtration and the like. The resultant crystal may be washed using the solvent used in the above-described reaction or the like, or may be dried. Thus obtained crude product of 9,9-bis(4-(2-hydroxyethoxy)phenyl)fluorene is usually a polymorph A, and its purity is usually 85% or more. Its purify is preferably 85% or more, more preferably 90% or more, further preferably 95% or more, for the purpose of obtaining substantially single polymorph B by crystallization described later. In the present invention, "substantially single" means single or that either polymorph A or polymorph B is contained in an amount of 10% by weight or less, preferably 5% by weight or less with respect to other crystal forms. In the case of the presence of other crystal polymorphs than the polymorph A or polymorph B herein described, the above-described proportions are used as references in all of other crystal polymorphs described.

The polymorph A in the present invention has at least one of the following features (a) to (c).

(a) The melt endotherm maximum by differential scanning calorimetry is 100 to 130° C., preferably 114 to 123° C., more preferably 116 to 120° C.

(b) The diffraction angle 2θ in a powder X-ray diffraction pattern by Cu—Kα line shows characteristic peaks at 7.9°, 11.6°, 12.7°, 14.2°, 17.4°, 18.7° and 21.8°.

(c) The bulk density is 0.2 to 0.4 g/cm$^3$.

Next, the method of dissolving the crude product of 9,9-bis(4-(2-hydroxyethoxy)phenyl)fluorene in at least one solvent selected from the group consisting of aromatic hydrocarbon solvents, ketone solvents and ester solvents, then, initiating deposition of 9,9-bis(4-(2-hydroxyethoxy)phenyl)fluorene at 50° C. or higher to produce the polymorph A of 9,9-bis(4-(2-hydroxyethoxy)phenyl)fluorene will be described.

Example of the aromatic hydrocarbon solvent include toluene, xylene, mesitylene and the like, examples of the ketone solvent include acetone, methyl ethyl ketone, methyl isobutyl ketone, cyclohexanone and the like, examples of the ester solvent include ethyl acetate, butyl acetate and the like, respectively. Preferable are toluene, xylene, acetone and ethyl acetate, more preferable are toluene and xylene, and further preferable is toluene. These solvents can be used as a mixture composed of two or more of them. Thought the use amount of the solvent is not particularly restricted providing 9,9-bis(4-(2-hydroxyethoxy)phenyl)fluorene deposits at 50° C. or higher, it is usually 0.5 to 20-fold by weight, preferably 1 to 10-fold by weight, further preferably 1.5 to 7-fold by weight with respect to 9,9-bis(4-(2-hydroxyethoxy)phenyl)fluorene. When the amount of the solvent is large, there occurs not only poor economy and poor productivity, but also an impossibility of a substantially single crystal form in some cases. When the amount of the solvent is small, there occurs not only an insufficient purification effect thereby increasing impurities, but also an impossibility of a substantially single crystal form in some cases.

Production of a crystal polymorph in the present invention is carried out by dissolving the crude product of 9,9-bis(4-(2-hydroxyethoxy)phenyl)fluorene in at least one solvent selected from the group consisting of aromatic hydrocarbon solvents, ketone solvents and ester solvents at a temperature higher than 50° C., then, cooling the resultant mixture to initiate deposition of a crystal of 9,9-bis(4-(2-hydroxyethoxy)phenyl)fluorene in the temperature range of 50° C. or higher and lower than the boiling point of the solvent (preferably, 60 to 100° C., more preferably 70 to 90° C.). Though the temperature in melting is not particularly restricted, it is usually 55° C. or higher and not higher than the boiling point of the solvent to be used, preferably 60 to 150° C., further preferably 70 to 110° C. When this temperature is lower, a substantially single crystal form cannot be obtained in some cases. After initiation of deposition of a crystal at 50° C. or higher, the mixture may be further cooled. Thought the temperature at the end of the cooling is not particularly restricted, it is usually −20 to 50° C., preferably 0 to 40° C., further preferably 10 to 30° C. When this temperature is lower, the purity tends to lower, and when this temperature is higher, the amount of loss into the solvent increases, to deteriorate economy and productivity. Though the cooling speed is not particularly restricted, it is usually 0.01 to 2° C., preferably 0.1 to 0.5° C. per minute. During the cooling, a crystal of 9,9-bis(4-(2-hydroxyethoxy)phenyl)fluorene is preferably added as a seed crystal into the mixture. In the case of addition of a crystal seed, it is preferable to add a crystal seed of a polymorph B in a metastable range width, for example, at temperatures lower by 1 to 10° C., preferably by 1 to 3° C. than the temperature of the saturated dissolution point of 9,9-bis(4-(2-hydroxyethoxy)phenyl)fluorene. The amount of the crystal seed to be added is 0.01 to 10% by weight, preferably 0.1 to 1% by weight, further preferably 0.3 to 0.7% by weight with respect to the crude product of 9,9-bis(4-(2-hydroxyethoxy)phenyl)fluorene.

The deposited crystal is recovered by filtration and the like. The resultant crystal may be washed with the solvent used or the like, or may be dried. Thus obtained crystal of 9,9-bis(4-(2-hydroxyethoxy)phenyl)fluorene is usually a polymorph B, and its purity is usually 95% or more.

The polymorph B in the present invention has at least one of the following features (d) to (f).

(d) The melt endotherm maximum by differential scanning calorimetry is 150 to 180° C., preferably 160 to 166° C., more preferably 163 to 165° C., particularly 164° C.

(e) The diffraction angle 2θ in a powder X-ray diffraction pattern by Cu—Kα line shows characteristic peaks at 12.3°, 13.5°, 16.1°, 17.9°, 18.4°, 20.4°, 21.0°, 23.4° and 24.1°.

(f) The bulk density is 0.5 or more, preferably 0.6 to 0.8 g/cm$^3$.

The present invention is capable of providing a novel crystal polymorph of 9,9-bis(4-(2-hydroxyethoxy)phenyl)fluorene maintaining a constant quality and excellent as a polymer raw material, and a method of producing the same. The polymorph B obtained by the present invention is advantageous for industrial handling from the standpoint of volume efficiency or the like since it has higher bulk density than known polymorphs A.

EXAMPLES

The present invention will be described specifically by examples and test examples shown below, but the present invention is not limited to them at all.

Example 1

Production of Crude Product

Into a glass reactor equipped with a stirrer, a nitrogen blowing tube, a thermometer and a water separator with cooling tube was charged 400 g of toluene and 3.25 g of phosphotungstic acid, and the mixture was azeotropically dehydrated under toluene reflux. To this was added 129.6 g (0.712 mol) of fluorenone, 994.9 g (7.20 mol) of 2-phenoxyethanol and 118.7 g of toluene, and the mixture was stirred for 21 hours while removing water generated by the reaction out of the system, under toluene reflux. To the resultant reaction mixture was added 1560 g of toluene, and the resultant mixture was adjusted to 70° C., and washed with 520 g of water four times. The resultant organic layer was concentrated under reduced pressure, to remove toluene and excess 2-phenoxyethanol. To the resultant mixture was added 1800 g of toluene, and 9,9-bis(4-(2-hydroxyethoxy)phenyl)fluorene was dissolved at 80° C., then, the resultant solution was decoloration-treated with activated carbon. The resultant solution was cooled gradually, to find initiation of deposition of a crystal at 42° C., and the solution was cooled down to 30° C. without any other procedure. The deposited crystal was taken out by filtration, and the crystal was dried to obtain 280 g (yield: 88.8%, purity: 91.8%) of a white crystal of a crude product of 9,9-bis(4-(2-hydroxyethoxy)phenyl)fluorene. The resultant crystal had a melting point (melt endotherm maximum by differential scanning calorimetry) of 105° C., and a bulk density of 0.24 g/cm$^3$.

Example 2

Production of Polymorph B

A suspension composed of 80 g of the crude product of 9,9-bis(4-(2-hydroxyethoxy)phenyl)fluorene obtained in Example 1 and 640 g of toluene was heated at 90° C., and stirred for 1 hour at the same temperature to obtain a uniform solution. This solution was cooled to 80° C., and 0.4 g of 9,9-bis(4-(2-hydroxyethoxy)phenyl)fluorine (polymorph B) was added as a crystal seed, and the mixture was stirred at the same temperature for 2 hours to cause deposition of a crystal. This liquid was cooled down to 20° C. at a cooling speed of 0.2° C. per minute, and stirred at the same temperature for 1 hour, to cause further deposition of a crystal. The deposited crystal was taken out by filtration, and the crystal was dried under reduced pressure, to obtain 73.0 g (yield: 91.3%, purity: 99.2%) of a white crystal of 9,9-bis(4-(2-hydroxyethoxy)phenyl)fluorene. The resultant crystal had a melting point (melt endotherm maximum by differential scanning calorimetry) of 164.0° C., and a bulk density of 0.75 g/cm$^3$.

Example 3

Production of Crude Product

Into a glass reactor equipped with a stirrer, a nitrogen blowing tube, a thermometer and a water separator with cooling tube was added 86.4 g (0.48 mol) of fluorenone, 397.9 g (2.88 mol) of phenoxyethanol, 350 g of toluene and 4.3 g of phosphotungstic acid [(H$_3$PW$_{12}$O$_{40}$)] which had been dried under reduced pressure at 100° C. to remove crystal water, and the mixture was stirred for 12 hours while removing generated water out of the system, under toluene reflux. The resultant reaction liquid was analyzed by high performance liquid chromatography to find generation of 197.3 g (0.45 mol) of 9,9-bis(4-(2-hydroxyethoxy)phenyl)fluorene. To this reaction liquid was added 300 g of toluene, and water-washed at 80° C. using 100 g of water. The resultant organic layer was cooled gradually, to find initiation of deposition of a crystal at 12° C., and the organic layer was cooled down to 10° C. without any other procedure, and stirred for 12 hours. The deposited crystal was taken out by filtration, and the crystal was dried to obtain 158.0 g (yield: 75.1%, LC purity: 99.9%) of a white crystal of a crude product of 9,9-bis(4-(2-hydroxyethoxy)phenyl)fluorene. The resultant crystal had a melting point (melt endotherm maximum by differential scanning calorimetry) of 109° C., and a bulk density of 0.24 g/cm$^3$.

Example 4

Production of Crude Product

Into a glass reactor equipped with a stirrer, a nitrogen blowing tube, a thermometer and a water separator with cooling tube was added 86.4 g (0.48 mol) of fluorenone, 663.2 g (4.80 mol) of phenoxyethanol, 350 g of toluene and 4.3 g of silicotungstic acid [(H$_4$SiW$_{12}$O$_{40}$)] which had been dried under reduced pressure at 100° C. to remove crystal water, and the mixture was stirred for 8 hours while removing generated water out of the system, under toluene reflux. The resultant reaction liquid was analyzed by high performance liquid chromatography to find generation of 201.5 g (0.46 mol) of 9,9-bis(4-(2-hydroxyethoxy)phenyl)fluorene. To this reaction liquid was added 300 g of toluene, and water-washed at 80° C. using 100 g of water. The resultant organic layer was concentrated under reduced pressure to remove toluene and excess phenoxyethanol. To the resultant mixture was added 600 g of toluene, and the mixture was stirred for about 1 hour with heating at 80° C. to give a uniform solution, then, the solution was gradually cooled, to find initiation of deposition of a crystal at 38° C., and the solution was cooled down to room temperature without any other procedure. The deposited crystal was taken out by filtration, and the crystal was dried to obtain 162.1 g (yield: 92.0%, LC purity: 96.2%) of a white crystal of a crude product of 9,9-bis(4-(2-hydroxyethoxy)phenyl)fluorene. The resultant crystal had a melting point (melt endotherm maximum by differential scanning calorimetry) of 104° C., and a bulk density of 0.23 g/cm$^3$.

Example 5

Production of Polymorph B

A suspension composed of 80 g of the crude product of 9,9-bis(4-(2-hydroxyethoxy)phenyl)fluorene obtained in Example 4 and 640 g of toluene was heated at 90° C., and stirred for 1 hour at the same temperature to obtain a uniform solution. This solution was cooled gradually, to find initiation of deposition of a crystal at 65° C., and the solution was cooled down to 30° C. without any other procedure, and thermally insulated and stirred at the same temperature for 1 hour. The deposited crystal was taken out by filtration, and the crystal was dried under reduced pressure to obtain 70.4 g (yield: 88.0%, LC purity: 98.2%) of a white crystal of 9,9-bis(4-(2-hydroxyethoxy)phenyl)fluorene. The resultant crystal had a melting point (melt endotherm maximum by differential scanning calorimetry) of 163.5° C., and a bulk density of 0.70 g/cm$^3$.

Example 6

Production of Polymorph B

A suspension composed of 60 g of the crude product of 9,9-bis(4-(2-hydroxyethoxy)phenyl)fluorene obtained in Example 3 and 300 g of xylene was heated at 100° C., and stirred for 1 hour at the same temperature to obtain a uniform solution. This liquid was cooled gradually, to find initiation of deposition of a crystal at 70° C., and the liquid was cooled down to 10° C. without any other procedure, and thermally insulated and stirred at the same temperature for 1 hour. The deposited crystal was taken out by filtration, and the crystal was dried under reduced pressure to obtain 53.9 g (yield: 89.9%, LC purity: 99.5%) of a white crystal of 9,9-bis(4-(2-hydroxyethoxy)phenyl)fluorene. The resultant crystal had a melting point (melt endotherm maximum by differential scanning calorimetry) of 163.5° C., and a bulk density of 0.75 g/cm$^3$.

Comparative Example 1

Production of Polymorph A

A suspension composed of 120 g of the crude product of 9,9-bis(4-(2-hydroxyethoxy)phenyl)fluorene obtained by the method according to Example 4 and 600 g of methanol was stirred at 60° C. for 1 hour. During this procedure, the liquid kept suspended condition. This suspension was cooled down to 10° C., and filtrated, then, the resultant crystal was dried under reduced pressure to obtain 107.0 g (yield: 89.2%, LC purity: 98.7%) of a white crystal of 9,9-bis(4-(2-hydroxyethoxy)phenyl)fluorene. The resultant crystal had a melting point (melt endotherm maximum by differential scanning calorimetry) of 118.8° C., and a bulk density of 0.26 g/cm$^3$.

Example 7

Production of Polymorph B

A suspension composed of 80 g of 9,9-bis(4-(2-hydroxyethoxy)phenyl)fluorene (polymorph A) prepared in Comparative Example 1 and 400 g of toluene was heated at 95° C. to give a uniform solution, this solution was cooled to 80° C., and 0.4 g of 9,9-bis(4-(2-hydroxyethoxy)phenyl)fluorene (polymorph B) was added as a crystal seed, and the mixture was stirred at the same temperature for 1 hour to cause deposition of a crystal. This liquid was cooled gradually to 10° C., and thermally insulated and stirred at the same temperature for 1 hour, to cause further deposition of a crystal. The deposited crystal was taken out by filtration, and the crystal was dried under reduced pressure to obtain 73.0 g (yield: 91.2%, LC purity: 99.7%) of a white crystal of 9,9-bis(4-(2-hydroxyethoxy)phenyl)fluorene. The resultant crystal had a melting point (melt endotherm maximum by differential scanning calorimetry) of 164.0° C., and a bulk density of 0.78 g/cm$^3$. The Na content was 25 ppb, the Fe content was 32 ppb, and the heat-melted color (220° C./3 hr) was APHA10.

Example 8

Production of Polymorph B

A suspension composed of 50 g of a crystal (polymorph B) of 9,9-bis(4-(2-hydroxyethoxy)phenyl)fluorene prepared in Example 5 and 250 g of toluene was heated at 90° C., and stirred at the same temperature for 1 hour to give a uniform solution. This solution was cooled gradually, to find initiation of deposition of a crystal at 72° C., and the solution was cooled down to 10° C. without any other procedure, and thermally insulated and stirred at the same temperature for 1 hour. The deposited crystal was taken out by filtration, and the crystal was dried under reduced pressure to obtain 45.5 g (yield: 90.8%, LC purity: 98.9%) of a white crystal of 9,9-bis(4-(2-hydroxyethoxy)phenyl)fluorene. The resultant crystal had a melting point (melt endotherm maximum by differential scanning calorimetry) of 163.7° C., and a bulk density of 0.77 g/cm$^3$. The Na content was 107 ppb, the Fe content was 79 ppb, and the heat-melted color (220° C./3 hr) was APHA30.

Test Example 1

Figure 2:
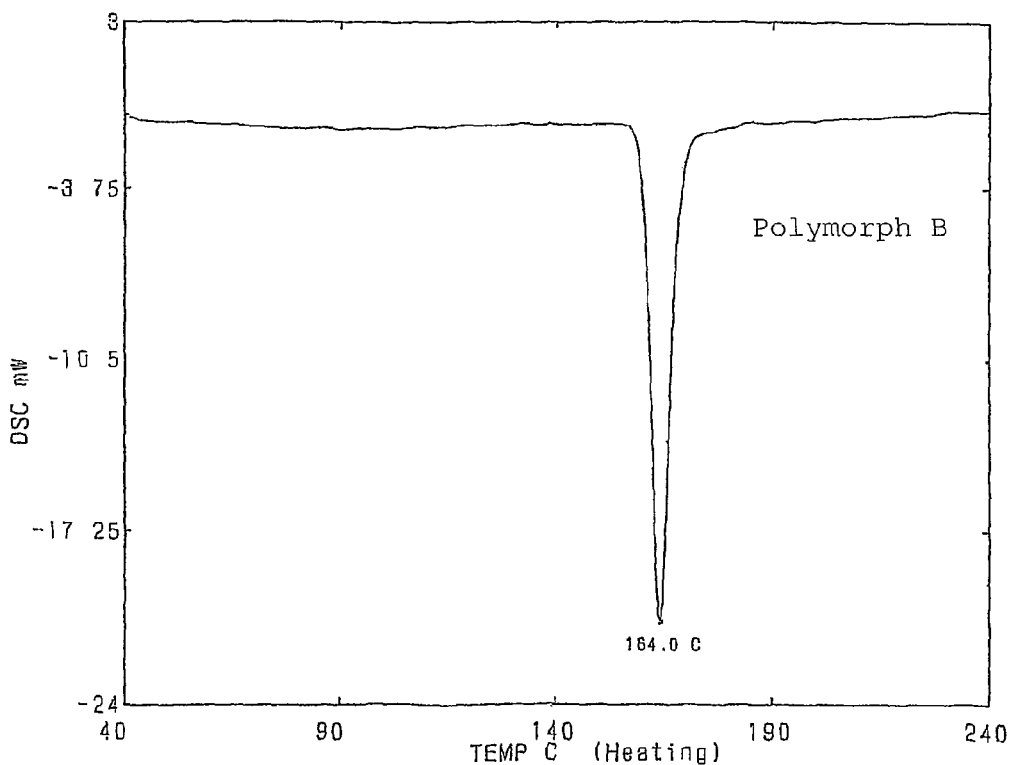
FIG. 2 is a view showing a differential scanning calorimetry (DSC) curve of a crystal (polymorph B) obtained in Example 2.

Differential Scanning Calorimetry (DSC) of Crystal Polymorph 10 mg of a crystal polymorph of 9,9-bis(4-(2-hydroxyethoxy)phenyl)fluorine and separately 10 mg of aluminum oxide were precisely weighed respectively in aluminum pans and measurement was performed under the following conditions using aluminum oxide as a subject using a differential scanning calorimeter (manufactured by Seiko Instruments Inc.: DSC220C). The results for the polymorph A obtained in Comparative Example 1 and for the polymorph B obtained in Example 2 are shown in FIG. 1 and FIG. 2, respectively.
(Operation Conditions)
Reagent: aluminum oxide
Temperature raising speed: 10° C./min
Measurement range: 40 to 260° C.
Atmosphere: open, nitrogen 40 ml/min

Test Example 2

Figure 3:
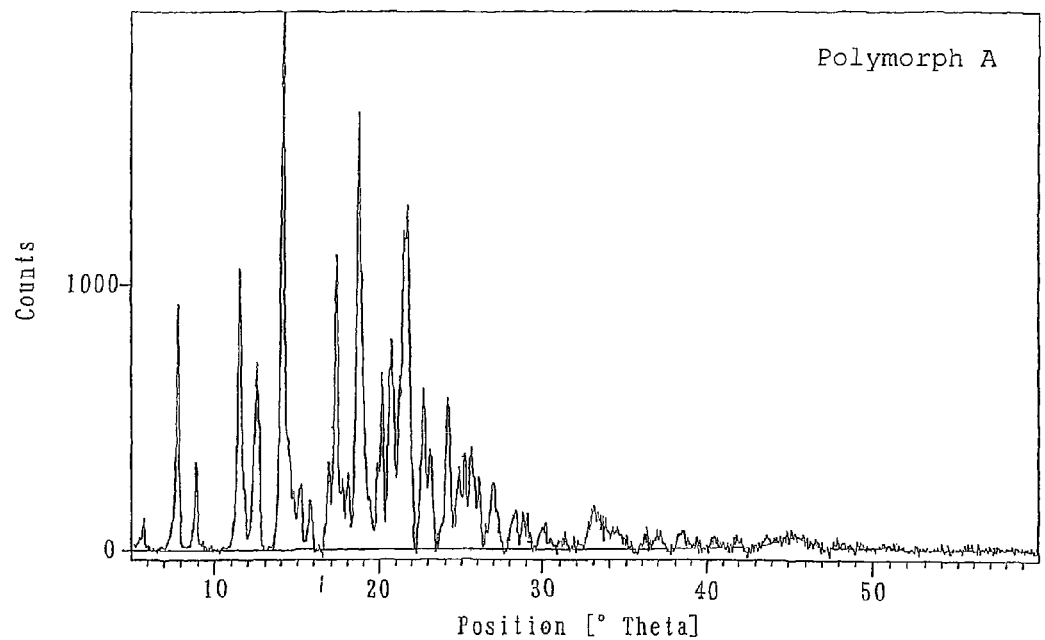
FIG. 3 is a view showing a powder X-ray diffraction pattern of a crystal (polymorph A) obtained in Comparative Example 1.
Figure 4:
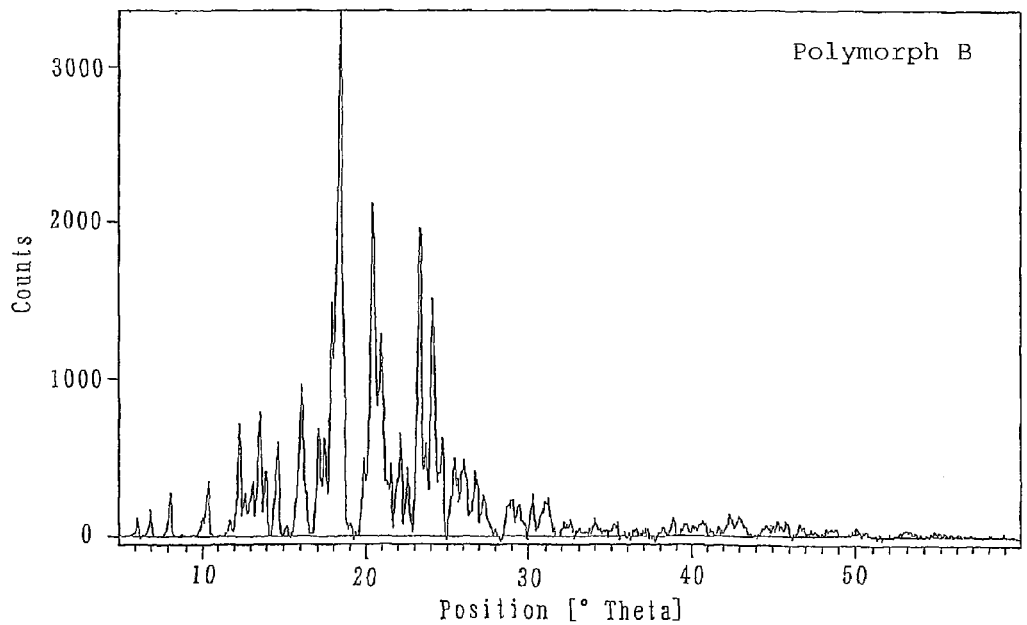
FIG. 4 is a view showing a powder X-ray diffraction pattern of a crystal (polymorph B) obtained in Example 2.

Powder X-ray Diffraction of Crystal Polymorph 150 mg of a sample was filled in a sample filling part of a glass test plate, and measured under the following conditions using a powder X-ray diffraction device (manufactured by Spectris Co., Ltd.: X'PertPRO). The results for the polymorph A obtained in Comparative Example 1 and for the polymorph B obtained in Example 2 are shown in FIG. 3 and FIG. 4, respectively.

X-ray source: CuKα
Output: 1.8 kW (45 kV-40 mA)
Measurement range: 2θ=5° to 60°
Scanning speed: 2θ=1.2°/min
Slit: DS=1°, mask=15 mm, RS=variable (0.1 mm to)

TABLE 1

| Analysis angle (2θ) | Relative intensity |
|---|---|
| 5.773 | 6 |
| 7.896 | 45 |
| 8.961 | 16 |
| 11.567 | 55 |
| 12.679 | 26 |
| 14.184 | 100 |
| 15.201 | 14 |
| 15.733 | 10 |
| 16.875 | 18 |
| 17.411 | 55 |
| 18.067 | 15 |
| 18.712 | 86 |
| 19.844 | 15 |
| 20.195 | 35 |
| 20.697 | 38 |
| 21.366 | 39 |
| 21.784 | 66 |
| 22.717 | 32 |
| 23.188 | 20 |
| 24.213 | 29 |
| 24.882 | 16 |
| 25.649 | 19 |
| 26.157 | 13 |
| 26.983 | 13 |
| 28.333 | 8 |
| 28.782 | 7 |
| 30.070 | 4 |
| 32.977 | 7 |
| 34.566 | 3 |
| 36.307 | 4 |
| 37.052 | 3 |
| 38.391 | 3 |
| 39.386 | 2 |
| 39.560 | 2 |
| 40.368 | 1 |
| 43.708 | 1 |
| 48.018 | 1 |
| 52.512 | 1 |

TABLE 2

| Analysis angle (2θ) | Relative intensity |
|---|---|
| 6.197 | 3 |
| 6.990 | 5 |
| 8.180 | 8 |
| 10.430 | 10 |
| 12.333 | 20 |
| 13.110 | 10 |
| 13.566 | 23 |
| 13.988 | 10 |
| 14.682 | 15 |
| 15.172 | 2 |
| 16.065 | 39 |
| 16.357 | 8 |
| 17.130 | 20 |
| 17.458 | 18 |
| 17.900 | 45 |
| 18.448 | 100 |
| 18.677 | 30 |
| 19.082 | 2 |
| 19.863 | 14 |
| 20.381 | 64 |
| 20.956 | 36 |
| 21.539 | 13 |
| 22.123 | 20 |
| 22.553 | 12 |
| 23.363 | 54 |
| 24.074 | 45 |
| 24.751 | 17 |
| 25.422 | 15 |
| 26.187 | 11 |
| 26.780 | 11 |
| 27.292 | 8 |
| 28.682 | 4 |
| 29.433 | 6 |
| 30.287 | 7 |
| 31.160 | 6 |
| 32.077 | 2 |
| 32.497 | 2 |
| 33.986 | 3 |
| 35.365 | 2 |
| 36.524 | 1 |
| 37.105 | 1 |
| 38.877 | 3 |
| 39.622 | 2 |
| 40.899 | 2 |
| 42.419 | 3 |
| 44.601 | 2 |
| 45.918 | 2 |
| 46.733 | 2 |
| 48.626 | 1 |
| 53.010 | 1 |

The invention claimed is:

1. A method of producing a crystal polymorph of 9,9-bis (4-(2-hydroxyethoxy)phenyl)fluorene, comprising the steps of
reacting fluorenone and 2-phenoxyethanol in the presence of a heteropolyacid,
initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene,
dissolving the crude product in at least one solvent selected from the group consisting of aromatic hydrocarbon solvents, ketone solvents and ester solvents, and
initiating deposition of 9,9-bis(4-(2-hydroxyethoxy)phenyl)fluorene at 50° C. or higher.

2. The production method according to claim 1, wherein the reaction of fluorenone and 2-phenoxyethanol in the presence of a heteropolyacid is carried out under dehydration condition.

3. The production method according to claim 1, wherein the heteropolyacid is a heteropolyacid constituted of phosphoric acid or silic acid, and of an oxyacid ion of at least one element selected from vanadium, molybdenum and tungsten.

4. The production method according to claim 1, wherein the heteropolyacid is a heteropolyacid anhydride or previously dehydration-treated heteropolyacid.

5. The production method according to claim 1, wherein the solvent is an aromatic hydrocarbon solvent.

6. The production method according to claim 1, wherein the solvent is toluene or xylene.

7. A crystal polymorph of 9,9-bis(4-(2-hydroxyethoxy) phenyl)fluorene, wherein the melt endotherm maximum by differential scanning calorimetry is 150 to 180° C.

8. A crystal polymorph of 9,9-bis(4-(2-hydroxyethoxy) phenyl)fluorene, wherein the melt endotherm maximum by differential scanning calorimetry is 160 to 166° C.

9. A crystal polymorph of 9,9-bis(4-(2-hydroxyethoxy)phenyl)fluorene, wherein the diffraction angle 2θ in a powder X-ray diffraction pattern by Cu—Kα line shows peaks at 12.3°, 13.5°, 16.1°, 17.9°, 18.4°, 20.4°, 21.0°, 23.4° and 24.1°.

10. The crystal polymorph according to claim 9, wherein the maximum peak of the diffraction angle 2θ is 18.4°.

11. A crystal polymorph of 9,9-bis(4-(2-hydroxyethoxy)phenyl)fluorene, obtained by reacting fluorenone and 2-phenoxyethanol in the presence of a heteropolyacid, initiating deposition of 9,9-bis(4-(2-hydroxyethoxy)phenyl)fluorene at lower than 50° C. from the resultant mixture to obtain a crude product of 9,9-bis(4-(2-hydroxyethoxy)phenyl)fluorene, dissolving the crude product in at least one solvent selected from the group consisting of aromatic hydrocarbon solvents, ketone solvents and ester solvents, and initiating deposition of 9,9-bis(4-(2-hydroxyethoxy)phenyl)fluorene at 50° C. or higher.

* * * * *